(12) United States Patent
Wimmer et al.

(10) Patent No.: US 9,351,630 B2
(45) Date of Patent: May 31, 2016

(54) FLEXIBLE ENDOSCOPE SHAFT, AND ENDOSCOPE WITH SAME

(71) Applicant: Karl Storz GmbH & Co. KG, Tuttlingen (DE)

(72) Inventors: Viktor Josef Wimmer, Seeon (DE); Robert Ayrenschmalz, Niederaichbach (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 105 days.

(21) Appl. No.: 14/080,121

(22) Filed: Nov. 14, 2013

(65) Prior Publication Data

US 2014/0142387 A1 May 22, 2014

(30) Foreign Application Priority Data

Nov. 15, 2012 (DE) .......................... 10 2012 022 442

(51) Int. Cl.
*A61B 1/00* (2006.01)
*A61B 1/005* (2006.01)

(52) U.S. Cl.
CPC ........... *A61B 1/0055* (2013.01); *A61B 1/00071* (2013.01); *A61B 1/00078* (2013.01)

(58) Field of Classification Search
USPC ................................. 600/121–125, 139–145
See application file for complete search history.

(56) References Cited

U.S. PATENT DOCUMENTS

| 779,374 | A | * | 1/1905 | Phillips ........................... 464/58 |
| 3,739,770 | A | * | 6/1973 | Mori ............................. 600/139 |
| 4,024,858 | A | * | 5/1977 | Chikama ........................ 600/139 |
| 4,329,980 | A | * | 5/1982 | Terada ........................... 600/144 |
| 4,776,844 | A | | 10/1988 | Ueda |
| 4,805,595 | A | * | 2/1989 | Kanbara ......................... 600/140 |
| 4,977,887 | A | * | 12/1990 | Gouda ........................... 600/144 |
| 5,176,660 | A | * | 1/1993 | Truckai .......................... 604/527 |
| 5,217,002 | A | * | 6/1993 | Katsurada et al. ............. 600/139 |
| 5,465,710 | A | * | 11/1995 | Miyagi et al. ................. 600/139 |
| 5,538,513 | A | * | 7/1996 | Okajima ........................ 604/527 |
| 5,746,696 | A | * | 5/1998 | Kondo ........................... 600/139 |
| 5,873,817 | A | | 2/1999 | Kokish et al. |
| 5,873,866 | A | * | 2/1999 | Kondo et al. .................. 604/526 |
| 5,927,345 | A | * | 7/1999 | Samson ......................... 138/127 |
| 6,107,004 | A | * | 8/2000 | Donadio, III ................. 430/320 |
| 6,485,411 | B1 | * | 11/2002 | Konstorum et al. ........... 600/139 |
| 6,520,214 | B1 | * | 2/2003 | Sugiyama et al. ............. 138/119 |

(Continued)

FOREIGN PATENT DOCUMENTS

| DE | 3714492 A1 | 11/1987 |
| DE | 4102211 A1 | 8/1991 |

(Continued)

*Primary Examiner* — Matthew J Kasztejna
(74) *Attorney, Agent, or Firm* — Whitmyer IP Group LLC

(57) ABSTRACT

A flexible endoscope shaft with a shaft body which, viewed in the longitudinal direction of the endoscope shaft, is composed of at least two shaft portions with different degrees of flexibility, wherein at least one shaft portion is composed of at least one spring element, and wherein all the spring elements of the shaft portions, which, viewed in the longitudinal direction of the shaft body, are arranged proximally from the outer distal shaft portion, are designed as reversibly deformable spring rods extending in the longitudinal direction of the shaft body. In order to create a flexible endoscope shaft that can be produced easily and cost-effectively, each of the shaft portions having at least one spring rod has at least one further spring rod, which is integrally bonded to the other spring rods of the respective shaft portion.

12 Claims, 3 Drawing Sheets

(56) References Cited

U.S. PATENT DOCUMENTS

| | | | |
|---|---|---|---|
| 7,850,604 B2 * | 12/2010 | Wimmer | 600/139 |
| 8,696,551 B2 * | 4/2014 | Miyagi et al. | 600/140 |
| 2005/0197536 A1 * | 9/2005 | Banik et al. | 600/179 |
| 2008/0300462 A1 | 12/2008 | Intoccia et al. | |
| 2009/0118584 A1 | 5/2009 | Kosuki et al. | |

FOREIGN PATENT DOCUMENTS

| | | |
|---|---|---|
| DE | 4317914 A1 | 12/1994 |
| DE | 19908152 A1 | 8/2000 |
| DE | 102004057481 A1 | 5/2006 |
| EP | 1658805 B1 | 8/2009 |
| EP | 2524645 A1 | 11/2012 |

* cited by examiner

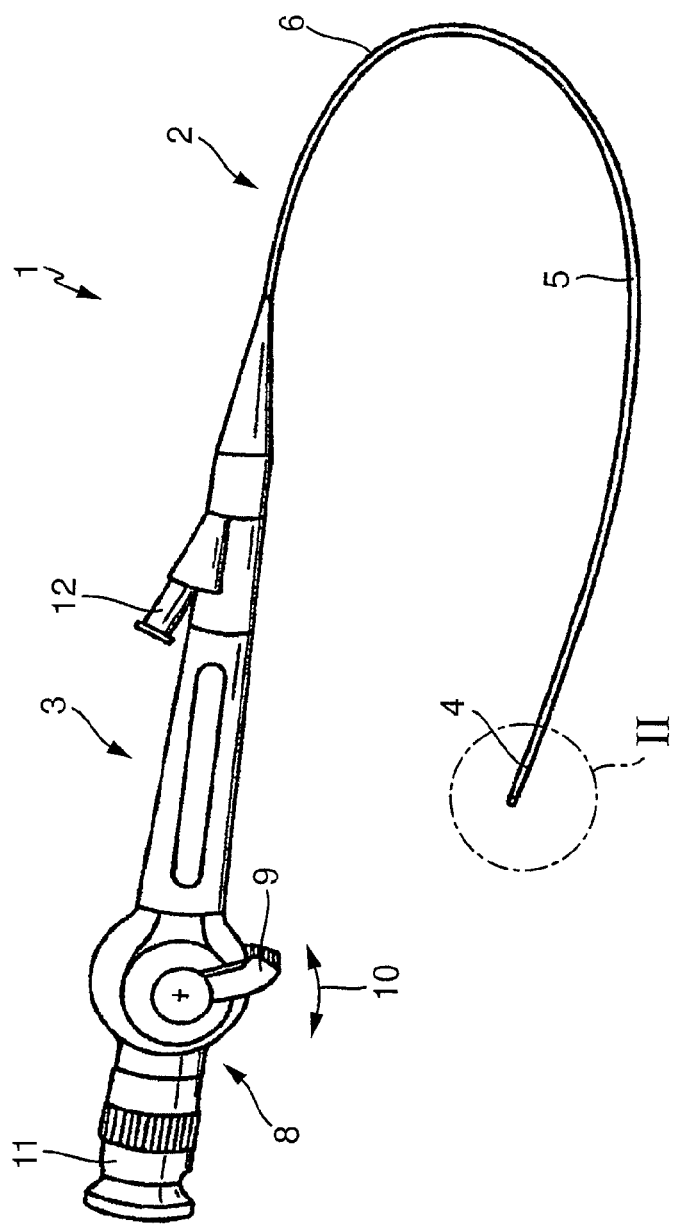
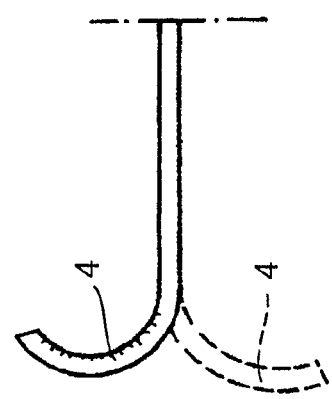

FLEXIBLE ENDOSCOPE SHAFT, AND ENDOSCOPE WITH SAME

FIELD OF THE INVENTION

The invention relates to a flexible endoscope shaft with a shaft body which, viewed in the longitudinal direction of the endoscope shaft, is composed of at least two shaft portions with different degrees of flexibility, wherein at least one shaft portion is composed of at least one spring element, and wherein all the spring elements of the shaft portions, which, viewed in the longitudinal direction of the shaft body, are arranged proximally from the outer distal shaft portion, are designed as reversibly deformable spring rods extending in the longitudinal direction of the shaft body. The invention further relates to an endoscope having a flexible endoscope shaft of the kind mentioned above.

BACKGROUND OF THE INVENTION

Flexible endoscopes, that is to say endoscopes with a flexible endoscope shaft, are used in medicine and for technical purposes, in order to examine branched or looped regions in the body or to examine machine parts.

Flexible endoscopes differ from rigid endoscopes in that the endoscope shaft of a flexible endoscope can adopt a bent, curved or even looped shape. By virtue of this flexibility of the endoscope shaft, flexible endoscopes are particularly suitable in medicine for operating on and examining regions in the body that have branched or looped structures, for example the gastrointestinal tract or the air passages.

Various approaches to the design of flexible endoscope shafts are known in practice.

DE 199 08 152 A1 discloses an endoscope, in the endoscope shaft of which flexible rods are arranged extending in the longitudinal direction. These flexible rods allow the operator to manually bend the endoscope shaft to a desired curved profile before the operation, such that the endoscope shaft can be advanced to the examination site through an opening in the body. On account of the stiffness of the rods, the endoscope shaft permanently maintains this predefined curved profile during use.

Although this stiffness of the flexion rods, which permit the shaping of the endoscope shaft, ensures an inner stiffness of the endoscope shaft, as is important for the use, it also limits the possible applications of a flexible endoscope of this design, since the predefined curved profile of the endoscope shaft cannot be changed during the operation, for example in order to examine lateral branches or the like.

A flexible endoscope of the type in question is known from EP 1 658 805 B1. In this known flexible endoscope, the endoscope shaft is composed of several shaft portions, which are each formed by a helical spring. The degree of flexibility of the individual shaft portions can be individually adjusted by the choice of different helical springs. The reversibly deformable helical springs of this known endoscope permit a flexible endoscope shaft that can be adjusted in each desired direction even during the examination.

Designing the spring elements of the individual shaft portions as helical springs has the disadvantage that cleaning the narrow helical-spring threads is quite complex. In addition, the production of the different helical springs is very elaborate and cost-intensive.

SUMMARY OF THE INVENTION

Proceeding from this, the object of the invention is to create a flexible endoscope shaft that is of the kind mentioned at the outset and that can be produced simply and cost-effectively.

According to the invention, this object is achieved by virtue of the fact that, viewed in the longitudinal direction of the shaft body from the distal end to the proximal end, each of the shaft portions having at least one spring rod has at least one further spring rod, which is integrally bonded to the other spring rods of the respective shaft portion.

By designing the spring elements as spring rods made from flat or round spring wire, the shaft body can be produced simply and cost-effectively.

In order to increase the dimensional stability and torsional stiffness of the individual shaft portions toward the proximal end of the shaft body, each shaft portion, viewed in the longitudinal direction of the shaft body from the distal end to the proximal end, has at least one additional spring rod, which is integrally bonded, in particular by laser welding, to the other spring rods, wherein the at least one additional spring rod of the respective shaft portion is arranged laterally on the spring rod coming from the previous shaft portion.

In a practical embodiment of the invention, it is proposed that the at least one further spring rod, extending in the longitudinal direction of the shaft body, is arranged laterally on the other spring rods of the respective shaft portion.

Furthermore, the invention proposes that each shaft portion of the shaft portions arranged proximally from the outer distal shaft portion, when viewed in the longitudinal direction of the shaft body, has at least two spring rods, each of which has a longitudinal extent reaching as far as the proximal end of the shaft body. The use of at least two spring rods for the non-distal shaft portion permits the design of a shaft body that has a sufficient bending strength and shear stability.

Furthermore, the invention proposes that the spring rods of each shaft portion are wound helically about each other and/or are wound helically about the spring rods of the shaft portions which, viewed in the longitudinal direction of the shaft body, are located distally. This helical winding of the spring rods about each other increases the dimensional stability, bending strength and torsional stability of the shaft portions. In order to fix the spring rods to each other in the position in which they are wound about each other, and in order to prevent the winding from coming undone, it is furthermore proposed that the spring rods wound helically about each other are integrally bonded to each other at some areas, preferably punctual, preferably by laser welding, wherein the properties of the individual shaft portions can be varied by means of the spring rods, wound about each other, being welded to each other only at a few locations or at many locations.

Winding the spring rods about each other also has the advantage that, upon bending of the endoscope shaft, there is no preferred bending direction, and instead the endoscope shaft can be bent with approximately the same force in all directions.

According to the invention, the properties of the individual shaft portions, for example in respect of the degree of flexibility and the bending strength, can be varied, inter alia, by virtue of the fact that the spring rods of the individual shaft portions are wound with the same or a different number of windings about the spring rods of the shaft portions which, viewed in the longitudinal direction of the shaft body, are located distally or proximally. More windings per unit of length result in a stiffening of the shaft portion, whereas fewer windings per unit of length make the respective shaft portion more flexible.

According to a preferred embodiment of the invention, it is proposed that the degree of flexibility of the spring elements of the individual shaft portions decreases from the distal end to the proximal end, that is to say the outer distal shaft portion is the most flexible, and the shaft portions become increasingly stiffer toward the proximal end of the shaft body.

According to a further embodiment according to the invention, it is proposed that the outermost distal shaft portion is composed of individual segments connected to each other in an articulated manner.

For pivoting the outer distal shaft portion, the invention proposes that the outermost distal shaft portion is pivotable via a pull mechanism, preferably at least one Bowden cable, engaging on the distal shaft portion.

For the design of the finished endoscope shaft, the invention proposes that all the shaft portions can be enclosed by an elastic outer sheath, preferably a hose.

The invention furthermore proposes that work channels, extending in the longitudinal direction of the shaft body, are arranged in the outer sheath, for example for receiving optical components, additional medical instruments, electrical lines and the pull mechanism.

The invention further relates to a flexible endoscope having a flexible endoscope shaft constructed in the manner described above.

BRIEF DESCRIPTION OF THE DRAWINGS

Further features and advantages of the invention will become clear from the appended drawings, in which a number of illustrative embodiments of a flexible endoscope shaft according to the invention are shown only by way of example, without limiting the invention to these illustrative embodiments. In the drawings:

FIG. 1 shows an overall view of an endoscope with a flexible shaft;

FIG. 2 shows an enlarged view of the detail II from FIG. 1 in different working positions;

DETAILED DESCRIPTION OF THE INVENTION

Figure 3:
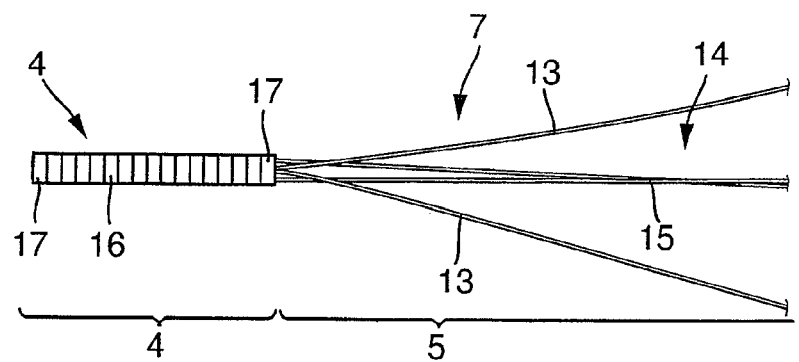
FIG. 3 shows an enlarged and schematic detailed view of part of the distal and middle shaft portion of a flexible endoscope shaft according to the invention.

The illustration in FIG. 1 shows a flexible endoscope 1 with a long flexible endoscope shaft 2, at the proximal end of which a handle 3 is arranged.

The flexible shaft 2 has a distal shaft portion 4, a middle shaft portion 5, and a proximal shaft portion 6. Work channels (not shown) are arranged in the endoscope shaft 2 and are used, for example, to receive optical fibers of the endoscope optics system, electrical lines and/or medical instruments.

As will be seen from FIG. 2, the outermost distal shaft portion 4 is particularly flexible and is able to pivot in different directions. The pivoting of the distal shaft portion 4 is effected via a pull mechanism 7 (shown in FIGS. 3 and 4) and a control device 8 arranged on the handle 3, which control device 8, in the illustrative embodiment shown in FIG. 1, is designed as an adjustment lever 9, which is adjustable in the direction of the arrows 10.

The handle 3 also has, at the proximal end, an eyepiece 11 and, at the distal end of the handle 3, a work channel entrance 12 through which, for example, a medical instrument can be introduced into a work channel of the endoscope shaft 2.

As will be seen from FIG. 2, the distal shaft portion 4 of the endoscope shaft 2 can be deflected up and down through almost 180° from the straight-ahead position shown in FIG. 1. Further deflections of up to 210°, and deflections of the distal shaft portion 4 in more than just two directions, are also possible.

The deflection of the distal shaft portion 4 is effected via a pull mechanism 7, which engages on the distal shaft portion 4 and which, in the embodiment shown in FIG. 3, is composed of two Bowden cables 13 secured on the distal shaft portion 4, which Bowden cables 13 are secured at the proximal end on the control device 8 of the handle 3. By actuation of the adjustment lever 9 of the control device 8 in the direction of the arrows 10, the distal shaft portion 4 is pivoted up or down in the desired direction.

For deflecting the distal shaft portion 4 in more than two directions, the control device 8, in an alternative embodiment of the endoscope 1, has two adjustment levers 9: one adjustment lever 9 for pivoting the distal shaft portion 4 up and down, and one adjustment lever 9 for pivoting the distal shaft portion 4 to the right and left. With these two adjustment levers 9, all directions are then also possible by combination of these pivoting directions.

The structure of the shaft portions 4, 5 and 6 is described in more detail below with reference to the illustrations in FIGS. 3 to 5.

To give the endoscope shaft 2 the required flexibility and at the same time sufficient bending strength and shear stability, all the shaft portions 5, 6 arranged proximally from the outer distal shaft portion 4, when viewed in the longitudinal direction of the shaft body, have reversibly deformable spring elements 14.

Figure 4:
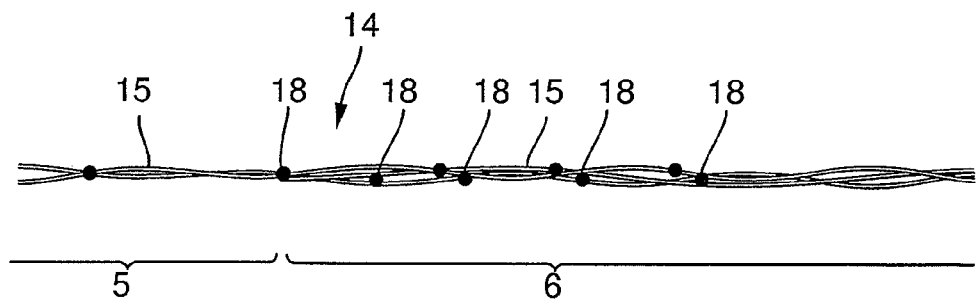
FIG. 4 shows an enlarged and schematic detailed view of part of the middle and proximal shaft portion of a flexible endoscope shaft according to the invention.
Figure 5:
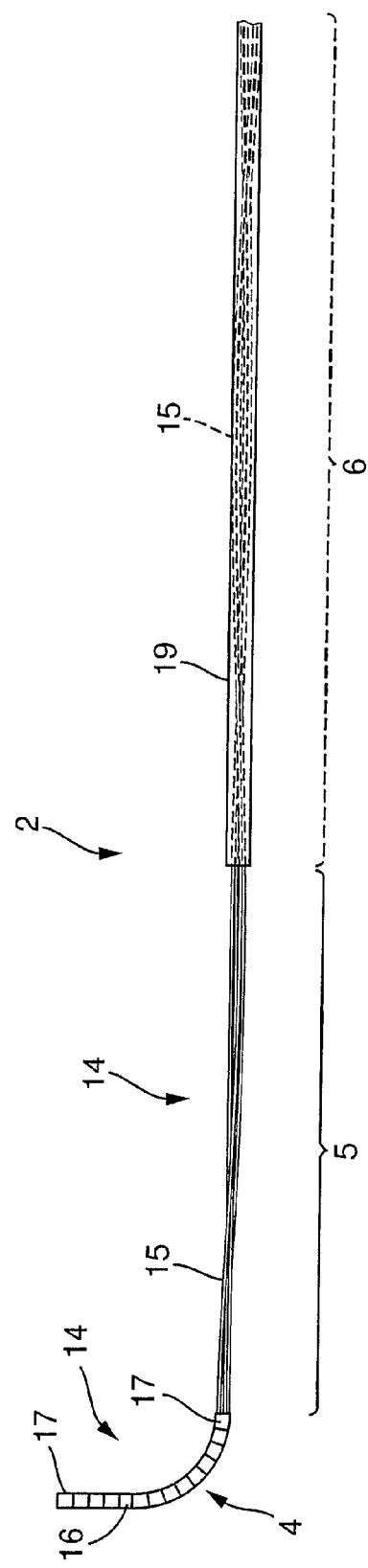
FIG. 5 shows a side view of part of a flexible endoscope shaft according to the invention with an outer sheath partially pushed onto it.

In the embodiments shown in the illustrations in FIGS. 3 to 5, all spring elements 14 of the shaft portions 5, 6 arranged proximally from the outer distal shaft portion 4, when viewed in the longitudinal direction of the shaft body, are designed as reversibly deformable spring rods 15 extending in the longitudinal direction of the shaft body.

In all of the embodiments shown, the outermost distal shaft portion 4 is composed of individual segments 16 connected to each other in an articulated manner.

In the embodiment shown in FIG. 3, the distal shaft portion 4, for attachment to the pull mechanism 7, is mounted between two Bowden cable holders 17 at the distal end and proximal end, wherein the proximal Bowden cable holder 17 serves as an abutment for the Bowden cable sheath, while the Bowden cable itself is mounted on the distal Bowden cable holder 17. By actuation of the control device 8 on the handle 3, the distal shaft portion 4 can in this way be pivoted up and down.

The middle shaft portion 5 of this depicted embodiment is composed of two spring rods 15, which are integrally bonded to the proximal Bowden cable holder 17 of the distal shaft portion 4. As will also be seen from FIG. 4, the two spring rods 15 of the middle shaft portion 5 are wound helically about each other and, further on in the longitudinal direction of the middle shaft portion 5, are connected to each other and mutually fixed at some areas, preferably punctual, by weld spots 18. The integral bonding of individual spring rods 15 to each other is preferably effected by means of laser welding.

By means of the spring rods 15 being wound helically about each other, the bending strength and torsional stability of the shaft portions 5, 6 so configured are increased. Winding the spring rods 15 about each other also has the advantage that, upon bending of the endoscope shaft 2, there is no preferred bending direction, and instead the endoscope shaft 2 can be bent with approximately the same force in all directions.

The illustration in FIG. 4 shows an enlarged and schematic detailed view of part of the middle shaft portion 5 and of the proximal shaft portion 6, as can be used for the design of the distal shaft portion 4 described above with reference to the illustration in FIG. 3.

At the transition to the proximal shaft portion 6, a third, additional spring rod 15 is integrally bonded to the two spring rods 15 of the middle shaft portion 5, preferably by means of laser welding. As will also be seen from FIG. 4, the additional spring rod 15 of the proximal shaft portion 6, extending in the longitudinal direction of the shaft body, is arranged laterally on the spring rods 15 coming from the previous middle shaft portion 5 and is wound helically about the two spring rods 15 of the middle shaft portion 5 and, further on in the longitudinal direction of the proximal shaft portion 6, they are connected to each other and mutually fixed at some areas, preferably punctual, by weld spots 18.

For designing the spring elements 14 designed as spring rods 15, both flat and also round metal springs, preferably of spring steel, can be used. Round spring rods 15 have the advantage that they have no preferential direction upon bending, whereas flat spring rods 15 are able to be easily bent only in two directions.

In the illustrative embodiments shown, the endoscope shaft 2 is composed of three shaft portions 4, 5 and 6. Alternatively, it is of course also possible for the shaft to be constructed from just two shaft portions or from more than three shaft portions. The structure of the individual shaft portions is advantageously such that the degree of flexibility of the individual shaft portions decreases from the distal end to the proximal end, starting from the most flexible, distal shaft portion 4, that is to say the shaft portions become increasingly less flexible or stiffer.

The degree of flexibility of the individual shaft portions 5 and 6 relative to each other can be adjusted by the choice of material and the geometry (length, shape, diameter) of the spring rods 15, the number of the spring rods 15 and/or the number of the windings of the spring rods 15 about each other and/or the number and position of the weld spots 18.

The helical winding of the spring rods 15 about each other can be configured in each shaft portion 5, 6 with the same number or a different number of windings, and with the same pitch or a different pitch of the windings. More windings per unit of length result in a stiffening of the shaft portion 5 or 6, whereas fewer windings per unit of length make the respective shaft portion 5 or 6 more flexible.

The use of the spring rods 15 as spring elements 14 permits simple and cost-effective production of the flexible endoscope shaft 2, such that the latter can even be produced and used as a disposable article.

As is shown schematically in FIG. 5, the shaft portions 4, 5 and 6 can be enclosed by an elastic outer sheath 19, preferably a hose. This outer sheath 19 then surrounds the spring elements 14 and segments 16, and also the work channels arranged coaxially with respect to the spring elements 14. The outer sheath 19 is advantageously designed such that the work channels, extending in the longitudinal direction of the endoscope shaft 2, are formed directly in the material of the outer sheath 19, as a result of which the assembly of the endoscope shaft 2 is made much easier.

According to an alternative embodiment of the endoscope shaft, the spring elements 14 and segments 16, and also the work channels arranged coaxially with respect to the spring elements 14, are covered by a kind of net stocking, which is then encased subsequently by the outer sheath 19.

A flexible endoscope shaft 2 constructed in the manner described above is characterized in that, while being of a simple design and being able to be produced cost-effectively, it has the required flexibility, in particular in the distal shaft portion 4, at the same time with sufficient bending strength, shear stability and torsional stability.

| List of reference signs | |
|---|---|
| 1 | endoscope |
| 2 | endoscope shank |
| 3 | handle |
| 4 | distal shank portion |
| 5 | middle shank portion |
| 6 | proximal shank portion |
| 7 | pull mechanism |
| 8 | control device |
| 9 | adjustment lever |
| 10 | arrow |
| 11 | eyepiece |
| 12 | work channel entrance |
| 13 | Bowden cable |
| 14 | spring element |
| 15 | spring rod |
| 16 | segment |
| 17 | Bowden cable holder |
| 18 | weld spot |
| 19 | outer sheath |

The invention claimed is:

1. A flexible endoscope shaft with a shaft body which, viewed in a longitudinal direction of the endoscope shaft, comprises:
   at least two shaft portions with different degrees of flexibility;
   wherein at least one shaft portion is composed of at least one spring element, and wherein all spring elements of the shaft portions, which, viewed in the longitudinal direction of the shaft body, are arranged proximally from an outer distal shaft portion, and are designed as at least two reversibly deformable straight rods extending in the longitudinal direction of the shaft body and wound helically about each other;
   wherein, viewed in the longitudinal direction of the shaft body from a distal end to a proximal end, each of the shaft portions having at least two reversibly deformable straight rods has at least one additional reversibly deformable straight rod compared with a previous shaft portion having at least two reversibly deformable straight rods, the at least one additional reversibly deformable straight rod being integrally bonded to the at least two reversibly deformable straight rods of the respective shaft portion at a plurality of positions along respective lengths of the at least two reversibly deformable straight rods;
   wherein the at least one additional reversibly deformable straight rod, extending in the longitudinal direction of the shaft body, is arranged laterally on the at least two reversibly deformable straight rods of the respective shaft portion.

2. The flexible endoscope shaft as claimed in claim 1, wherein each of the at least two reversibly deformable straight rods has a longitudinal extent reaching as far as the proximal end of the shaft body.

3. The flexible endoscope shaft as claimed in claim 1, wherein the at least two reversibly deformable straight rods of each shaft portion are wound helically about the at least two reversibly deformable straight rods of the shaft portions which, viewed in the longitudinal direction of the shaft body, are located distally.

4. The flexible endoscope shaft as claimed in claim 3, wherein the at least two reversibly deformable straight rods of each shaft portion are integrally bonded to each other at a plurality of positions along respective lengths thereof.

5. The flexible endoscope shaft as claimed in claim 3, wherein the at least two reversibly deformable straight rods of each shaft portion are wound, with the same or a different number of windings, about the at least two reversibly deformable straight rods of the shaft portions which, viewed in the longitudinal direction of the shaft body, are located distally or proximally.

6. The flexible endoscope shaft as claimed in claim 1, wherein the degree of flexibility of the individual shaft portions decreases from the distal end to the proximal end.

7. The flexible endoscope shaft as claimed in claim 1, wherein the outermost distal shaft portion is composed of individual segments connected to each other in an articulated manner.

8. The flexible endoscope shaft as claimed in claim 1, wherein the outermost distal shaft portion is pivotable via a pull mechanism engaging on the distal shaft portion.

9. The flexible endoscope shaft as claimed in claim 1, wherein all the shaft portions can be enclosed by an elastic outer sheath, preferably a hose.

10. An endoscope, comprising:
a flexible endoscope shaft with a shaft body which, viewed in a longitudinal direction of the endoscope shaft, includes:
at least two shaft portions with different degrees of flexibility;
wherein at least one shaft portion is composed of at least one spring element, and wherein all spring elements of the shaft portions, which, viewed in the longitudinal direction of the shaft body, are arranged proximally from an outer distal shaft portion, and are designed as at least two reversibly deformable straight rods extending in the longitudinal direction of the shaft body and wound helically about each other;
wherein, viewed in the longitudinal direction of the shaft body from a distal end to a proximal end, each of the shaft portions having at least two reversibly deformable straight rods has at least one additional reversibly deformable straight rod compared with a previous shaft portion having at least two reversibly deformable straight rods, the at least one additional reversibly deformable straight rod being integrally bonded to the at least two reversibly deformable straight rods of the respective shaft portion at a plurality of positions along respective lengths of the at least two reversibly deformable straight rods;
wherein the at least one additional reversibly deformable straight rod, extending in the longitudinal direction of the shaft body, is arranged laterally on the at least two reversibly deformable straight rods of the respective shaft portion.

11. The flexible endoscope shaft as claimed in claim 1, wherein the at least one additional reversibly deformable straight rod is integrally bonded to the at least one other reversibly deformable straight rod of the respective shaft portion by spot welds.

12. A flexible endoscope shaft, comprising:
a first shaft portion at a distal end of the endoscope shaft;
a second shaft portion and a third shaft portion at different longitudinal positions along the endoscope shaft, the second shaft portion being positioned between the first shaft portion and the third shaft portion;
wherein the second shaft portion includes a first number of reversibly deformable rods extending along a length of the second shaft portion, the third shaft portion includes a second number of reversibly deformable rods extending along a length of the third shaft portion, and the first number is less than the second number;
wherein at least two of the reversibly deformable rods of the second shaft portion are wound helically about one another other and are integrally bonded to one another at a plurality of positions along respective lengths thereof, and at least two of the reversibly deformable rods of the third shaft are wound helically about one another other and are integrally bonded to one another at a plurality of positions along respective lengths thereof.

* * * * *